(12) United States Patent
Derval et al.

(10) Patent No.: US 8,317,522 B2
(45) Date of Patent: Nov. 27, 2012

(54) HORMONAL QUOTIENT PROFILE CALCULATOR

(76) Inventors: Diana Derval, Amsterdam (NL); Johan Bremer, Amsterdam (NL)

( * ) Notice: Subject to any disclaimer, the term of this patent is extended or adjusted under 35 U.S.C. 154(b) by 352 days.

(21) Appl. No.: 12/657,305

(22) Filed: Jan. 19, 2010

(65) Prior Publication Data

US 2011/0178437 A1    Jul. 21, 2011

(51) Int. Cl.
| | |
|---|---|
| G01B 1/00 | (2006.01) |
| A61B 1/00 | (2006.01) |
| A61B 5/103 | (2006.01) |
| A61B 5/117 | (2006.01) |
| A61B 5/00 | (2006.01) |
| G06C 27/00 | (2006.01) |
| G06G 1/02 | (2006.01) |
| G09B 1/00 | (2006.01) |
| G09B 1/02 | (2006.01) |
| G09B 19/00 | (2006.01) |
| G09B 25/00 | (2006.01) |

(52) U.S. Cl. ........... 434/404; 33/511; 33/512; 235/78 R; 235/83; 235/84; 434/195; 434/198; 434/199; 434/205; 434/206; 434/405; 600/300; 600/587

(58) Field of Classification Search ................. 600/300, 600/306, 557, 587; 33/403, 418, 452, 474, 33/476, 485, 511, 512; 434/195, 197, 198, 434/199, 205, 206, 215, 404, 405; 235/61 GM, 235/63 R, 63 E, 63 F, 63 G, 70 R, 70 A, 70 B, 235/70 C, 78 R, 78 F, 78 G, 78 M, 78 RC, 235/83, 84, 85 FC See application file for complete search history.

(56) References Cited

U.S. PATENT DOCUMENTS

| 4,456,821 A * | 6/1984 | Harter ........................ 235/78 R |
|---|---|---|
| 6,886,740 B1 * | 5/2005 | Craig ........................ 235/85 FC |
| 7,637,418 B2 * | 12/2009 | Craig ........................ 235/88 RC |
| 2008/0234552 A1 | 9/2008 | Averbach | |

* cited by examiner

*Primary Examiner* — Jeffrey G Hoekstra
*Assistant Examiner* — Devin Henson
(74) *Attorney, Agent, or Firm* — Magda Carvalho

(57) ABSTRACT

A hand held device (10) for measuring automatically the Hormonal Quotient and correlated hormonal status of an individual, providing a measure of index finger for ring finger. The device (10) includes a base (30) upon which a concentrically arranged disc (40) is rotatable mounted by a central fastener (11). The base (30) carries a ruler face (32), a first finger-length logarithm scale (36), a Hormonal Quotient logarithm scale (38) and an arrow indicator of the gonadal hormone exposure index (39). The disc (40) carries a second finger-length logarithm scale (42) and the Hormonal Quotient arrow (44). When scales (42) and (36) are properly aligned the Hormonal Quotient arrow (44) inserts automatically into the resulting Hormonal Quotient in the Hormonal Quotient scale (38) and the correlated gonadal hormone exposure (39). In an alternative embodiment, Hormonal Quotient symbols (60) on the base (30) represent the Hormonal Quotient result and are viewed through a window (50) in the disc while a panel (50) disposed between the base (30) and the disc (40) having two die cut windows (52), allows the individual to set the result for a specific gender.

4 Claims, 6 Drawing Sheets

US 8,317,522 B2

HORMONAL QUOTIENT PROFILE CALCULATOR

CROSS REFERENCE TO RELATED APPLICATIONS

This application claims the benefit of U.S. provisional application Ser. No 61/335,796 filed 2010 Jan. 11.

FEDERALLY SPONSORED RESEARCH

Not Applicable

SEQUENCE LISTING OR PROGRAM

Not Applicable

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

This application relates to slide rules and, more particularly to slide rulers which are used for diagnosing the 2D:4D ratio of an individual from the length of the index finger and the length of the ring finger and uses thereof.

BACKGROUND OF THE INVENTION

The ratio of the lengths of the index finger to the ring finger is called the 2D:4D ratio or digit ratio. The 2D:4D ratio of an individual is affected by exposure to androgens (gonadal hormones) e.g., testosterone or estrogen, while in the uterus. As such, the 2D:4D ratio has been suggested as an index for these two hormones which are associated with multiple human traits, phenotypes and conditions.

Hormones are chemicals released by cells which bring about intriguing biological connections because they affect the response of cells in other parts of an organism. As such, there has been an extensive amount of scientific research conducted on the 2D:4D ratio as an index for multiple human traits, phenotypes and conditions. Several studies have now shown that the 2D:4D ratio may correlate with and reveal variation of several human and non-human primate traits such as behavior, vocation, sensory, perception (taste, music), health (food preferences, hormonal related diseases), sexuality, dating and differential psychology (ability, cognition, and personality). The most well-know index for the 2D:4D ratio relates to differences between the sexes, it is on average lower in men than in women. Thus, the 2D:4D ratios has several applications in the business and medical fields and provides a non-invasive, simple and time-saving measure screening of multiple human traits, phenotypes and conditions.

Currently, the calculation of the 2D:4D ratio requires that the full length of both index finger and ring finger of the right hand be measured separately by using either a ruler or caliper. Then, the individual divides the length of the index finger by that length of the ring finger. The quotient 2D:4D is the digit ratio. Next, the individual searches the literature for the hormonal status e.g., gonadal hormone exposure index (testosterone or estrogen) that corresponds to his or her 2D:4D ratio. Any 2D:4D ratio smaller than 1 indicates a longer ring finger and is associated with exposure to testosterone, while a ratio larger than 1 indicates a longer index finger and is linked to exposure to estrogen. The problem with this process is that it is time-consuming and the operation (division) is error-prone when done on paper.

Slide rulers have been in use for a long time but some slide rules are extremely specialized for very narrow applications. An example of a slide ruler that solves a specific problem is a slide ruler to estimate the Body Mass Weight of an individual from its measurements of weight and height as described or disclosed by U.S. Patent Publication No. 2008/0234552 published Sep. 25, 2008 to Averbach.

In view of the above, a need remains for a unique device providing an almost instantaneous calculation of an individual's 2D:4D ratio and simultaneous visualization of corresponding hormonal status. Another need is that such device can be manually manipulated solely by the individual. Yet another need is that the device should be such that it can be used on a continued basis because the range of traits and conditions related to the 2D:4D ratio expands as scientific research develops. Still another need, requires that such device be simple, easy and affordable. Thus, a device solving the aforementioned problems is desired. The present invention is directed to fulfilling these needs.

SUMMARY OF THE INVENTION

The need remaining in the prior art is addressed by the present invention, which relates to a device for diagnosing an individual's 2D:4D ratio (Hormonal Quotient). This device may be equally used for other finger ratio. A device has been developed on which a combination of an individual's length of the ring finger and length of the index finger immediately indicates his or her Hormonal Quotient (2D:4D ratio) profile including simultaneous visualization of a gonadal hormone exposure index, e.g., estrogen or testosterone. Using this device, an individual can then determine a wealth of sex-dependent, hormonally influenced traits, phenotypes and conditions, which reach into the domains of behavior, vocation, sensory, perception (taste, music, vision, proprioception, balance, pain, temperature, smell and touch), nutrition, dating, hobbies, arts, fertility, health, physique, sexuality and also deeply into differential psychology (ability, cognition, and personality).

An exemplary device is comprised of a base, a top rotatable disc and a central fastener, and it is made of any suitable material. The disc and base are mounted for free rotation in either direction about their center fastener. In the preferred embodiment, the base carries indicia of a first finger-length scale according to a logarithmic equivalent to the measurement lengthwise of a finger, a Hormonal Quotient scale according to a logarithmic equivalent to the 2D:4D ratio and two arrow indicators of the gonadal hormone exposure index, and a ruler face. The top disc carries a second finger-length scale according to a logarithmic equivalent to the measurement lengthwise of a finger, and an arrow pointing to the Hormonal Quotient result in the Hormonal Quotient scale displayed on the base.

The scales and the arrow are arranged in a registered relationship, wherein the circumferential spaces are in radial alignment. For each variable, the scales are printed in such a way that when the applicable finger-length value for the index finger and that for the ring finger are correctly aligned, automatically the Hormonal Quotient arrow is at the correct position in the Hormonal Quotient scale according to the 2D:4D formula and simultaneously displays a category of the corresponding gonadal hormone exposure, e.g., testosterone or estrogen.

In an alternative embodiment, a coding system is utilized to represent the hormonal status range in place of both Hormonal Quotient scale and the indicators, a die cut window in the disc exposes the Hormonal Quotient result and a moving panel is placed between the disc and the base. The window of the disc exposes one of the graphic images of the coding system printed on the base. In one embodiment, the back side of the base contains information specific for each graphic image depicted on the front of the base. The procedural operation is similar to that described above.

The present invention provides a new device of using for diagnosing the Hormonal Quotient profile and simultaneous visualization of the hormonal status, e.g. gonadal hormone index, of an individual and one which has all the advantages of the prior art and none of the disadvantages of the prior art in assessing the 2D:4D ratio.

The present invention further provides a new device for diagnosing the Hormonal Quotient profile that is susceptible of low-cost of manufacturing, and which accordingly is susceptible of low price-of-sale to the consuming public, thereby making such a device economically available to the consuming public.

Another advantage of the present invention is that the device is portable, light-weight and easily fits into a purse, and or the like.

The Hormonal Quotient profile enables important hormonally influenced traits, conditions and phenotypes deficiencies to be identified for subsequent honing and improvement. The domains reached by the Hormonal Quotient profile include behavior, perception, fertility, health, nutrition, dating, physique, sexuality, dating, career counseling, hobbies, arts, sports and differential psychology (ability, cognition, and personality) which correspond to particular areas of scientific research. For that reason, approaches for remedying any trait deficiency or make use of a newly discovered trait can be selected from existing educational, medical, marketing, scientific and informational programs.

These together with other objects of the present invention, along with various features of novelty which characterize the invention, are pointed out with particularity in the claims annexed to and forming a part of this disclosure. For a better understanding of the invention and its operating advantages, and the specific objects attained by its uses, reference should be had to the accompanying drawings and descriptive matter.

DRAWINGS

Figures

The present invention is illustrated by way of example, and not of limitation, in the accompanying figures, in which like references indicate similar elements, and in which.

DETAILED DESCRIPTION

FIGS. 1, 2, 3 and 4

First Embodiment

In accordance with the teachings of the present invention, a device has been developed for individuals to calculate almost instantaneously their 2D:4D digit ratio and simultaneously visualize correlated hormonal status e.g., gonadal hormone exposure index. Throughout the course of the following discussion the 2D:4D digit ratio, or 2D:4D ratio, is referred to as Hormonal Quotient.

For the purposes of the current discussion, the embodiments of the present invention will be explained in terms of exemplary embodiments directed to a human; however the device may equally be used with several other animals including non-human primates (for example, monkeys, chimpanzee, gorilla or orangutan), mammals (for example, mice,), birds (for example, zebra finch). The device may equally be used for all possible digit ratio, for example, 1D:2D, 1D:3D, 1D:3D, 1D:5D, 2D:3D, 2D:5D, 3D:4D, 3D:5D and 4D:5d. The device may also apply for the digital ratio of the toes. While these exemplary embodiments are described in sufficient detail to enable those skilled in the art to practice the present invention, it should be understood that other embodiments may be realized, and that changes may be made without departing from the spirit and scope of the invention. It is to be understood that the below examples are merely illustrative of the inventive methodology. Thus, the following detailed description is presented for purposes of illustration only and not of limitation, and the scope of the invention is defined solely by the appended claims.

As noted above, the formula which is used to determine the Hormonal Quotient (i.e., 2D:4D digit ratio) of an individual involves a division. The length of the index finger is divided by the length of the ring finger.

As noted above, the formula which is used to determine the Hormonal Quotient (2D:4D ratio) of an individual involves a division. The length of the index finger is divided by the length of the ring finger.

Figure 1:
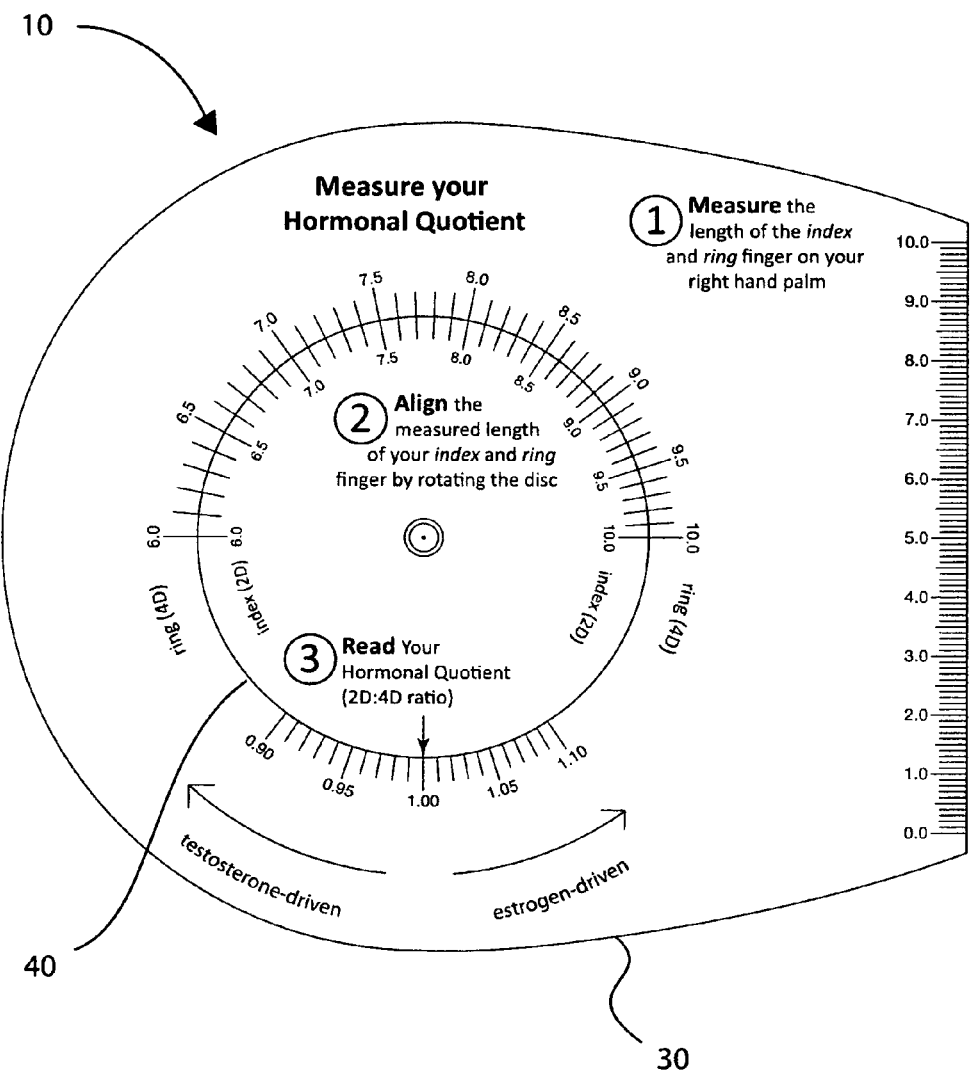
FIG. 1 is a plain view of the preferred embodiment of the device, showing the base and the disc in a properly registered position for use.
Figure 2:
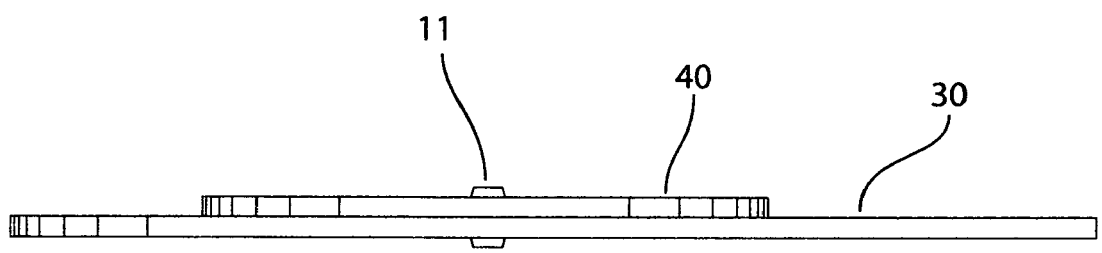
FIG. 2 is a vertical sectional view taken centrally through the device of FIG. 1 shows the stacked arrangement of the base and the top disc.

FIG. 1 illustrates an exemplary hand held device 10 for automated calculation of a Hormonal Quotient profile and simultaneous visualization of correlated hormonal status e.g., estrogen-driven or testosterone-driven of an individual. Device 10 is made of, but not limited to, paper, cardboard, steel, wood, leather or plastic or any other suitable material and it may be opaque, transparent or semi-opaque and of flexible material or rigid material. The system used by device 10 is based on the metric units of measurement which is more accurate than the imperial units of measurement; however, conversion of the system to the imperial units of measurement is also applicable. An exemplary device 10 is semicircular-straight shaped, as illustrated in FIG. 1, but any other shape or geometric form and or any size may be used. In one embodiment, the shape of device 10 is straight, as opposed to circular, slide rule. In another embodiment, the shape of device 10 takes the form of a barrel with a tape. Device 10 is planar and comprises a fixed base 30, a rotatable disc 40 and a central fastening means 11. Base 30 and disc 40 are rotatable mounted by central fastening means 11 as illustrated in FIG. 2. Disc 40 and base 30 are mounted for free rotation in either direction about their center fastener 11. Fastening means 11 are passed through the common axis points thereof as illustrated in FIG. 2 and is preferably a rivet.

Figure 3:
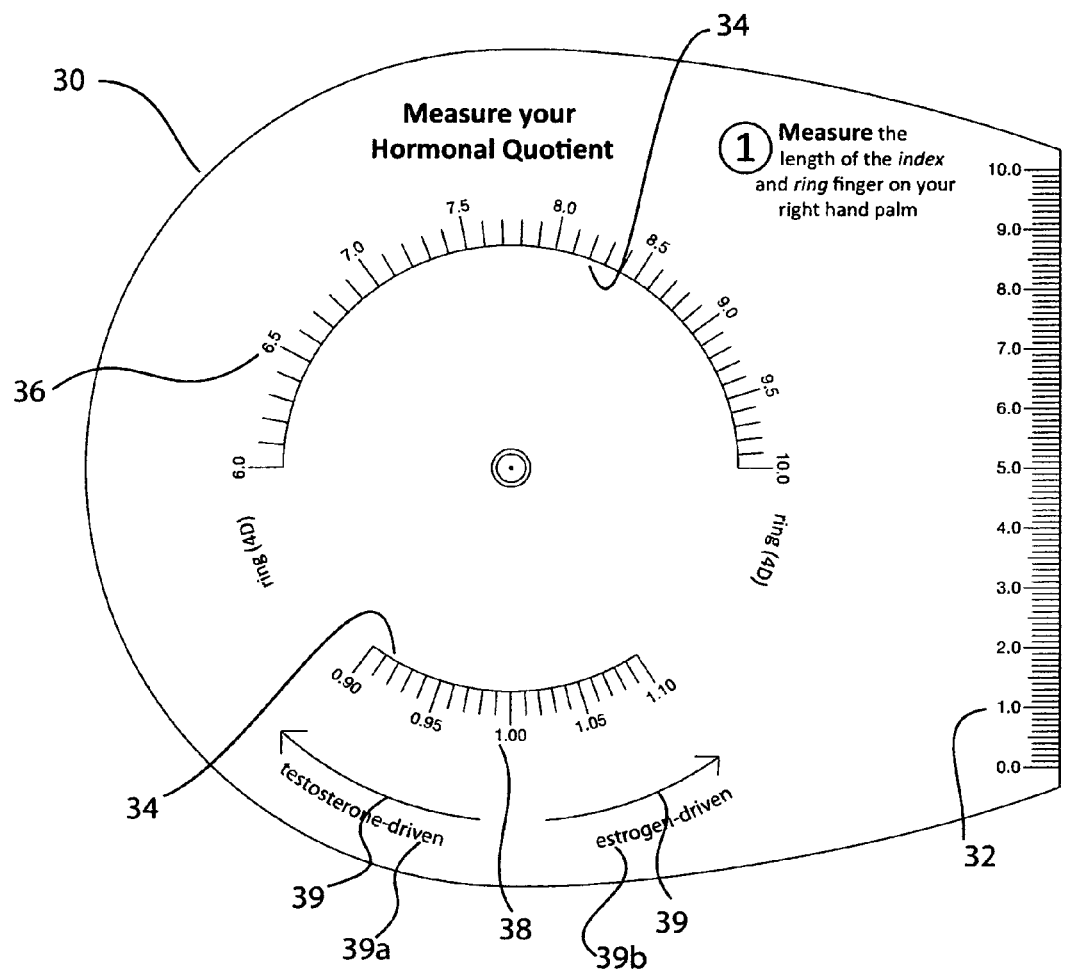
FIG. 3 is a plain view of the base.

Base 30 is shown in FIG. 3 as circular-rectangular shaped having one rounded edge carrying an annular concentric band 34 and an opposite straight edge which disposes a ruler face 32. Base 30 has sufficient space to have printed thereon a comprehensive set of operating instructions. Ruler 32 is used to determine the actual length of both index finger and ring finger. Ruler 32 is 10 cm long and has a row of numerical values from 0 cm to 10 cm for measuring purposes employing the conventional metric units of measurement. The metric ruler deals with centimeters (abbreviated cm) and millimeters (abbreviated mm). The larger lines with numbers are centimeters (cm), and the smallest lines are millimeters (mm). as shown in FIG. 1. As such, by using ruler 32 on the base 30. since millimeters are $\frac{1}{10}$th of a centimeter, if the user measures his finger length 2 marks after 6 centimeter (cm), it is 6.2 centimeters long. In one embodiment, ruler 32 further includes graduations of inches, half inches, quarter inches, and eighth inches (i.e., imperial system). The row of numbers on ruler 32 is imprinted, etched or otherwise applied to thereon such that the numbers can he viewed from the top face of ruler 32.

Annular concentric band 34 has a diameter of about 13.5 cm. Band 34 has indicia formed partially about its periphery portion that projects outwardly beyond the circumferential edge of the smaller in diameter disc 40 thereabove. The top periphery of band 34 carries a first finger-length scale 36 according to a logarithmic equivalent to the measurement lengthwise of a finger. In the preferred embodiment, first finger-length scale 36 is dedicated to the length of the index finger; however, the ring finger can be used, in which case the index finger is used with a second finger-length scale 42. First finger-length scale 36 has a row of appropriately-spaced numbers from six to ten and includes a smaller stripe for half numbers and an even smaller stripe for each tenth of a number and has a range encompassing the largest and smallest sizes of fingers which are likely to exist in humans.

The logarithmic scale used to position the finger-length scale 36 is as follows $(180*(\log(x)-\log(6)))/(1-\log(6))$ for x the numbers from 6 to 10 can be filled in, and the result of the formula is the rotation in degrees of the stripe, given that zero degrees corresponds to a stripe pointing left, ninety degrees to a stripe pointing up, and one-hundred-eighty degrees to a stripe pointing right. All logarithms are base-10.

The bottom periphery of band 34 carries a Hormonal Quotient scale 38 according to a logarithmic equivalent to the 2D:4D ratio and two arrows indicators 39 of a hormonal status, e.g., the gonadal hormone exposure index. Hormonal Quotient scale 38 is numbered from 0.90 to 1.10 as illustrate in FIG. 3; however various other ranges may be used.

The logarithmic scale used to position the Hormonal Quotient scale 38 is as follows $270-((180*\log(x))/(1-\log(6)))$ and the resulting rotation in degrees is used the same as described above. So for 0.90 this would result in a rotation of about 307.12 degrees and for 1.10 the rotation is about 236.41 degrees.

One of the arrow indicators of gonadal hormone exposure index 39 carries a legend for testosterone 39a while the other arrow indicator carries a legend for estrogen 39b, each corresponding to a given result in the Hormone Quotient scale 38. Arrow indicators of gonadal hormone exposure index 39 are shown as two arrows symmetrically pointed to opposite directions away from a 1.00 mark which are printed alongside such Hormonal Quotient scale 38. Arrow indicator 39 for testosterone-driven 39a is numbered from lesser than 1 to 0.90 in a clockwise direction away from the 1 mark and arrow indicator 39 for estrogen-driven 39b is numbered from more than 1 to greater than 1.10 in a counterclockwise direction away from 1 mark.

In one embodiment, both arrow indicators 39 and legends 39a and 39b are replaced by a correlation of the dominance of testosterone and estrogen in relation for anthropometric, behavioral, nutritional, health-related, occupational, dating, vocation, perception, fertility, marketing, dating or any applicable variable. In another embodiment, there are two separated windows, one window shows indicia of index for females (showing both estrogen and testosterone results), and the other shows indicia for males (showing both estrogen and testosterone results) in relation for anthropometric, behavioral, nutritional, health-related (prevention and advise), vocational, team-building, couching, education orientation, gift advise, dating, perception or fertility variables and market segmentation, recruitment, career couching. In yet another embodiment, there is a plurality of windows encompassing indicia (estrogen and testosterone) specifically designed for each ethnic group and or in relation to the variables described above.

Figure 4:
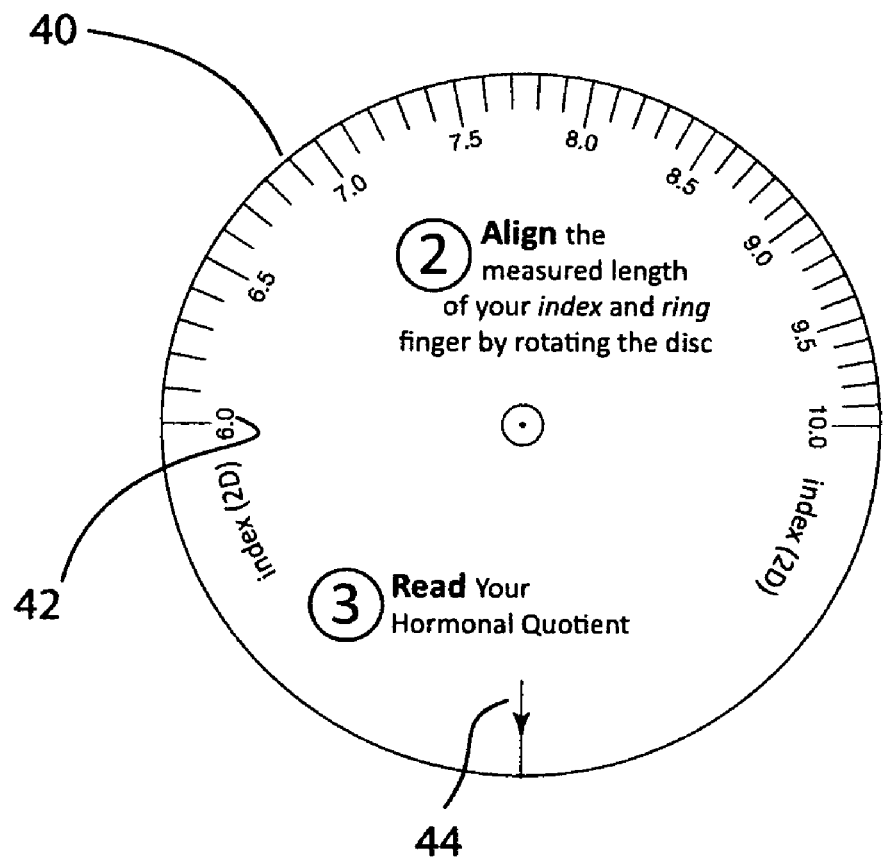
FIG. 4 is a plain view of the top rotating disc.

Disc 40 as illustrated in FIG. 4 has a smaller diameter than band 34 and is disposed immediately above thereof. Disc 40 has sufficient space to have printed thereon a comprehensive set of operating instructions. The top periphery of disc 40 carries second finger-length scale 42 according to the logarithmic equivalent to the measurement lengthwise of a finger and has printed thereon a row of nine appropriately-spaced numbers and includes a smaller stripe for half numbers and an even smaller stripe for each tenth of a number, which has a range encompassing the largest and smallest sizes of fingers which are likely to exist in humans. In the preferred embodiment, second finger-length scale 42 is dedicated to the length of the index finger; however, the ring finger may be used, in which case the index finger is used with first scale 36. The bottom periphery of disc 40 carries a Hormone Quotient arrow 44 pointing to the Hormonal Quotient result in Hormonal Quotient scale 38 displayed on the bottom periphery of band 34 printed on base 30.

As is evident from the description and drawings above, first finger-length scales 36 and Hormonal Quotient scale 38 on band 34 and second finger-length scale 42 and arrow 44 on disc 40 are arranged in a registered relationship, wherein the circumferential spaces are in radial alignment. For each variable, scales 36, 38 and 42 are printed in such a way that when the applicable finger-length value for the index finger of scale 42 and the applicable finger-length value for the ring finger of scale 36 are aligned, simultaneously Hormonal Quotient arrow 44 is at the correct position in Hormonal Quotient scale 38 according to the 2D:4D ratio formula.

Operation—FIG. 1

The use of device 10 of the present invention may now be understood. In the preferred embodiment, the fingers of the right hand are used. The index and ring fingers are measured with fingers straight from the bottom crease where the finger joins the hand to the tip of the finger. The bottom crease of the finger is to be placed under the 0 cm of ruler 32. The first step of the process is to measure the full length of the ring finger with ruler 32. The known numerical value of the length of the ring finger is then found in scale 36 on band 30. Next, the individual measures the full length of the index finger with ruler 32. The known numerical value of the length of the index finger is then found in scale 42 of disc 40. Then, the individual rotates disc 40 such that the numerical value of the index finger exactly juxtaposes that numerical value of the ring finger on scale 36. This step inserts Hormonal Quotient arrow 44 into the resulting Hormonal Quotient in Hormonal Quotient scale 38 and the corresponding gonadal hormonal exposure index 39 is simultaneously visualized as a particular level of testosterone-driven 39a or estrogen-driven 39b. For example, alignment of scale 42 for an index finger measuring 6.2 cm with scale 36 for a ring finger of 6.4 cm, Hormonal Quotient arrow 44 shows automatically the Hormonal Quotient as around 0.97 and simultaneously a high hormone testosterone-driven status.

Figure 5A:
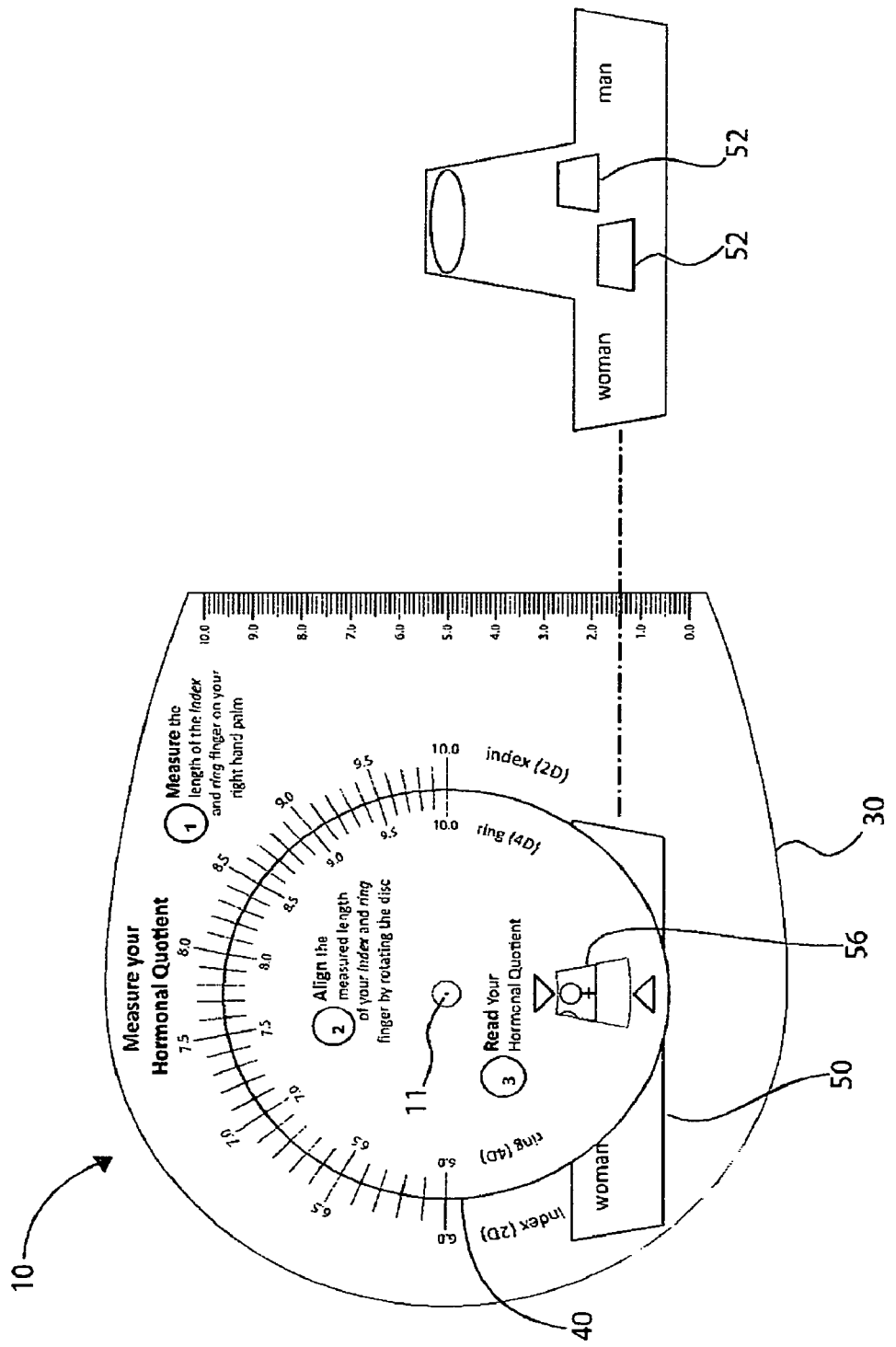
FIGS. 5A and 5B show the device of FIG. 1 in accordance with alternative embodiments, with addition of multiple cut die windows and use of symbols, and showing in a partially exploded plain view a moving panel positioned between the base and the disc.

Now referring to FIG. 5A, window 56 of disc 40 is predetermined to align with each die cut window 52 of panel 50. Panel 50 lies immediately beneath disc 40 and above base 30 and is generally rectangular at the bottom with straight edges and has an extended area in the middle adapted to be secured by the fastener 11; however panel 50 may have a different shape or form. Panel 50 is predetermined in such a way as to move in either direction along with the two stripes of Hormonal Quotient symbols 60 on base 30. The edges of panel 50 extend beyond the circumferential. edge of disc 40 and are thus easily arranged for turning and are forcibly manually displaceable from a set male position to female position when desired. Panel 50 has two die cut gender windows 52 appropriately spaced apart, one at the bottom and the other at the top, each one is predetermined for viewing one of the graphic images 60 on base 30. Each die cut window 52 of the panel 50 cooperates with window 56 of disc 40 to expose only one Render symbol 60 printed on the base 30, as shown in FIG. SA. In the preferred embodiment, the bottom window 52 is dedicated to females while the top window 52 is dedicated to males; however any other arrangement may he used as well.

It is evident that device 10 may use first finger-length scale 36 on base 30 for the index finger and second finger-length scale 42 on disc 40 for the ring finger and that the specific procedure is similar to that described above.

Figure 5B:
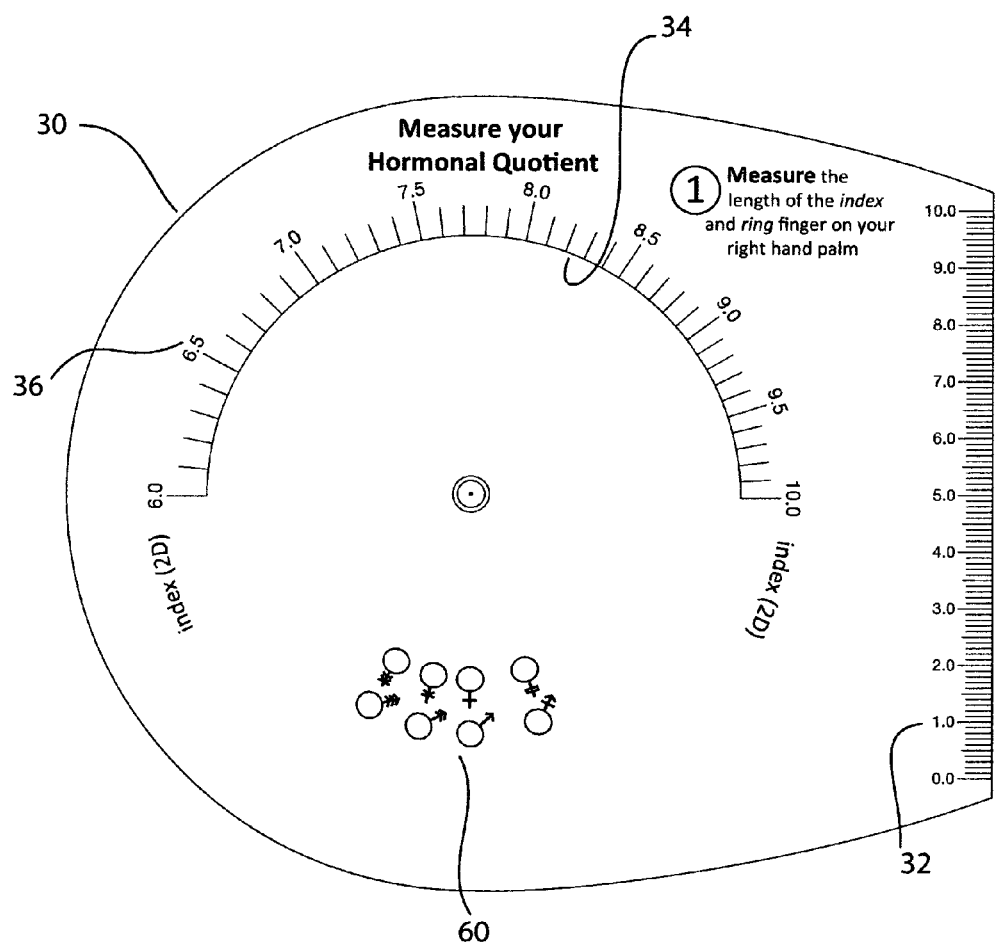

FIGS. 5A and 5B—Additional Embodiments

FIGS. 5A and 5B show additional, of the several possible, embodiments of this application, the option here being the use of Hormonal Quotient symbols 60 representing a coding system for the hormonal status range in the form of icons or graphic images printed at the bottom portion of base 30, as illustrated in FIG. 5B, in place of Hormonal Quotient scale 38 and arrow indicators 39 and legends 39a and 39b. There is no Hormonal Quotient arrow 44 on disc 40, instead a die cut viewing window 56 in disc 40, as illustrated in FIG. 5A, is used to expose the Hormonal Quotient result. A moving panel 50, as illustrated in FIG. 5A, is now provided positioned between disc 40 and base 30.

Now referring to FIG. 5B, the bottom of base 30 has printed thereon Hormonal Quotient symbols 60 representing the hormonal status range obtained from the Hormonal Quotient result (i.e., 2D:4D digit ratio). Symbols 60 as illustrated in FIG. 5B are gender symbols in the form of the conventional female symbol (i.e., circle with a cross at the bottom) or male symbol (i.e., circle with an arrow sticking out and to the right). Additional indicia affixed to the line segment of the circle of each gender symbol create gender symbols 60 which are utilized to map overall the hormonal status index. F.ach such indicia is in the form of a stroke (bar) or an open triangle (headed anow)Each gender symbol 60, also herein named Hormone Quotient symbol 60 stands for a different category and subgroups of the gonadal hormone index level (i.e.. hormonal status) i.e., estrogen-driven or testosterone-driven. The symbols 60 are arranged in a particular sequence, in an incremental way from the center, a clockwise and a counterclockwise direction, as shown in FIG. 5B. With respect to testosterone-driven, as shown in FIG. 5B the direction of progression of the symbols in increasing fashion is clockwise from the center (the center is testosterone and estrogen balanced). The estrogen-driven is positioned at the right end.

Now referring to FIG. 5A, window 56 of disc 40 is predetermined to expose one of the Hormonal Quotient symbol 60 printed on base 30. Panel 50 lies immediately beneath disc 40 and above base 30 and is generally rectangular at the bottom with straight edges and has an extended area in the middle adapted to be secured by the fastener 11; however panel 50 may have a different shape or form. Panel 50 is predetermined in such a way as to move in either direction along with the two stripes of Hormonal Quotient symbols 60 on base 30. The edges of panel 50 extend beyond the circumferential edge of disc 40 and are thus easily arranged for turning and are forcibly manually displaceable from a set male position to female position when desired. Panel 50 has two die cut gender windows 52 appropriately spaced apart, one at the bottom and the other at the top, each one is predetermined for viewing one of the graphic images 60 on base 30. In the preferred embodiment, the bottom window 52 is dedicated to females while the top window 52 is dedicated to males; however any other arrangement may be used as well.

Now referring to FIG. 5B, the bottom of base 30 has printed thereon Hormonal Quotient symbols 60 representing the hormonal status range obtained from the Hormonal Quotient result. Symbols 60 as illustrated in FIG. 5B are in the form of the conventional female symbol (circle with a cross at the bottom) or male symbol (circle with an arrow sticking out and to the right). Additional indicia affixed to the line segment of the circle of each gender's symbol are utilized to map overall the hormonal status index. Each such indicia is in the form of a stroke (bar) or an open triangle (headed arrow), each Hormone Quotient symbol 60 stands for a different hormonal status, e.g., estrogen-driven or testosterone-driven.

An exemplary code of Hormonal Quotient symbols 60, as illustrated in FIG. 5B, has the following correlations. Regarding males, two and three headed arrow corresponds to testosterone-driven while a stroke corresponds to estrogen-driven. Specifically, the male symbol 60 with three headed arrows shows that the individual was influenced by higher levels of prenatal testosterone. The male symbol 60 with two headed arrows shows that the individual was influenced by medium levels of prenatal testosterone. And the male symbol 60 with a stroke shows that the individual was influenced by estrogen. While the conventional male symbol 60 shows that the individual was influenced equally by prenatal testosterone and estrogen levels. Regarding females, a double stroke corresponds to estrogen-driven, while one headed arrow and double headed arrow correspond to testosterone-driven. Specifically, the female symbol 60 with double headed arrows shows that the individual was influenced by higher levels of prenatal testosterone. The female symbol 60 with one headed arrow shows that the individual was influenced by medium levels of prenatal testosterone. The female symbol 60 with double stroke shows that the individual was influenced by prenatal estrogen. The conventional female symbol 60 shows that the individual was influenced equally by estrogen and testosterone. In another code example (not shown), the capital letter "T" is used for testosterone dominance and the capital letter "E" for estrogen dominance. However, any other coding system is equally used as well and any pictorial representation, picture, symbol, icon, insignia or other appropriate depiction including any color-coding could be used. In one embodiment, arrow indicator gonadal hormone. index 39 and or corresponding legends 39a and 39h and or numerical values corresponding to Hormonal Quotient scale 38 arc concurrently presented with Hormonal Quotient symbols 60. Hormonal Quotient scale 38 are concurrently presented with Hormonal Quotient symbols 60.

Hormonal Quotient symbols 60 are arranged into two rows disposed in parallel fashion to one another, the top row representing male while the bottom row representing female;

however it can have any other arrangement. Symbols 60 are divided evenly into radial spaces to be appropriately viewable through windows 56 and 52 when scales 36 and 42 are aligned as desired.

In one embodiment, the back side of base 30 contains information accompanying each symbol 60 depicted on the front of base 30 identifying the hormonal status and or any other correlation and or directing the user to a particular website, book or the like.

In operation, with reference to FIGS. 5A and 5B, after window 52 is set for the desired gender, i.e., female gender symbol (circle with a cross at the bottom) or male sender symbol (circle with an arrow sticking out and to the right), which are depicted on the bottom of the fixed base 30 as shown in FIG. 5B, then operation of the alternate embodiment is similar to that of device 10. In the alternative embodiment one symbol 60 is viewable through windows 56 and 52.

Conclusion, Ramifications, and Scope

Thus in accordance with this invention is now possible to almost instantaneously calculate a Hormonal Quotient profile of an individual. While exemplary drawings and the presently preferred embodiments of the present invention have been described and illustrated, it is to be understood that the scope of the present invention is not to be limited to the particular embodiments discussed. Thus, the embodiments shall be regarded as illustrative rather than restrictive, and it should be understood that various changes can be made therein by workers skilled in the arts without departing from the scope of the present invention as set forth in the appended claims and structural and functional equivalents thereof.

We claim:

1. An algorithmic slide rule for diagnosing a 2D/4D digit ratio of an individual based upon a measure of the index finger by a measure of the ring finger, comprising:
   a. a fixed base having printed thereon a first finger-length scale juxtaposed to entries on a second finger-length scale on a top rotating disc, a hormonal quotient scale, a hormonal status indicator, and a ruler face, said ruler face being of the metric system, said first finger-length scale on said base represents a logarithmic equivalent to a measure lengthwise of a ring or index finger of said individual;
   b. said top rotating disc having a smaller diameter than said base and coaxially mounted on top of said base provided with said second finger-length scale juxtaposed to entries on said first finger-length scale on said base, and a hormonal quotient arrow pointing to said hormonal quotient scale and to said hormonal status indicator, said second finger-length scale on said disc represents a logarithmic equivalent to a measure lengthwise of a ring or index finger of said individual;
   whereby when the individual measures the length of said ring finger and said index finger on said ruler face and aligns the value of the measured length of said ring finger on the first finger-length scale with the value of the measured length of said index finger on the second finger-length scale, said hormonal quotient arrow automatically moves to a hormonal quotient result in said hormonal quotient scale with simultaneous visualization of the resulting hormonal status.

2. The algorithmic slide rule of claim 1, wherein said hormonal status indicator on said base includes prenatal gonadol hormones obtained from said 2D/4D digit ratio.

3. An algorithmic slide rule diagnosing a 2D/4D digit ratio of an individual based upon a measure of the index finger by a measure of the ring finger, comprising:
   a. a fixed base having printed thereon a first finger-length scale according to a logarithm scale equivalent to a length of a finger juxtaposed to entries on a second finger-length scale on a top rotating disc, two rows of a plurality of gender symbols printed in an upper row and a lower row in parallel fashion to one another, and a ruler face, said ruler face being of the metric system, said first finger-length scale on said base represents a logarithmic equivalent to a measure lengthwise of a ring or index finger of said individual;
   b. a rectangular moving panel with straight edges and a centered projection extending upwards to be secured by a fastener, being positioned between said base and said top disc, being smaller than said base and said top disc with said straight edges protruding from said top disc, having a two die cut windows separated from each other therein for gender selection, each said die cut window being predetermined and disposed to expose only one said symbol on said base upon alignment of said symbol with one said die cut window, each said die cut window adapted to cooperate with a window in said top rotating disc to expose said only one symbol, said panel being independently movable relative to said base and said top disc;
   c. said top rotating disc coaxially mounted on top of said panel provided with said second finger-length scale according to a logarithm scale equivalent to a length of a finger juxtaposed to entries on said first finger-length scale on said base, and having said window to view said symbol on said base upon alignment with said each die cut window in said panel, said second finger-length scale represents a logarithmic equivalent to a measure lengthwise of a ring or index finger of said individual;
   whereby when said die cut window in said panel is selected for one of said gender symbols and the individual measures the length of said ring finger and said index finger on said ruler face and aligns the value of the measured length of said ring finger on the first finger-length scale with the value of the measured length of said index finger on the second finger-length scale, said window in said top disc automatically displays one said symbol.

4. The algorithmic slide rule of claim 3, wherein each said gender symbol printed on said base includes a plurality of indicia affixed thereon, each said symbol corresponding to a particular level of a gonadal hormone obtained from said 2D/4D digit ratio, said symbols being arranged in a particular sequence.

* * * * *